United States Patent [19]

Stier et al.

[11] Patent Number: 4,601,899
[45] Date of Patent: Jul. 22, 1986

[54] HYDROUS TOOTHPASTE CONTAINING TIF$_4$ AND CHELATING AGENT

[75] Inventors: Roger E. Stier, Clifton, N.J.; William H. Dunn, Brooklyn, N.Y.; James D. Vidra, Lebanon, N.J.

[73] Assignee: Beecham Inc., Clifton, N.J.

[21] Appl. No.: 716,552

[22] Filed: Mar. 27, 1985

[51] Int. Cl.$^4$ .......................... A61K 7/18; A61K 33/16
[52] U.S. Cl. ........................................ 424/52; 424/151
[58] Field of Search .................................. 424/52, 151

[56] References Cited

U.S. PATENT DOCUMENTS

| | | | |
|---|---|---|---|
| 3,751,568 | 8/1973 | Mundorff et al. | 424/52 |
| 3,885,028 | 5/1975 | Cella et al. | 424/52 |
| 4,157,387 | 6/1979 | Benedict | 424/52 |
| 4,291,017 | 9/1981 | Beierle et al. | 424/52 |
| 4,418,053 | 11/1983 | Muhler et al. | 424/52 |

*Primary Examiner*—Shep K. Rose
*Attorney, Agent, or Firm*—Jacobs & Jacobs

[57] ABSTRACT

An extrudable, shape-retaining aqueous toothpaste which comprises an anti-caries effective amount of TiF$_4$, a dental polishing or abrasive agent, a chelating agent in an amount effective to stabilize the TiF$_4$, and an aqueous dental vehicle, said aqueous toothpaste having a pH of at least about 3.5.

15 Claims, No Drawings

HYDROUS TOOTHPASTE CONTAINING TIF$_4$ AND CHELATING AGENT

The present invention relates to toothpaste containing an anti-caries effective amount of TiF$_4$.

Titanium tetrafluoride has been reported as providing greater reduction of enamel solubility and greater protection against animal caries than comparable levels of other fluorides, as well as forming a glaze on the teeth. Shresta et al., Enamel Dissolution: I. Effects of Various Agents and Titanium Tetrafluoride, J. Dent. Res. 51, 1561-1566, 1972 and II. Action of Titanium Tetrafluoride, J. Dent. Res. 51, 1567-1571, 1972. In the patent literature, TiF$_4$ is used in the form of a 1% aqueous solution having a pH of about 1.5, see, e.g. Mundorf et al., U.S. Pat. No. 3,751,568, but this highly acidic solution may result in marked irritation to the mouth unless carefully applied, and hence the use of TiF$_4$ has been suggested for annual or semiannual applications of a 1% aqueous solution of TiF$_4$ by a dentist. Prior efforts to provide TiF$_4$ in other than the highly acidic 1% solution have not been successful, because TiF$_4$ is unstable in aqueous media at a pH above 3.0, and this coupled with its potential for irritation, has prevented the use of TiF$_4$ in consumer products.

The present invention now provides a toothpaste having a pH of about 3.5 or more, comprising an aqueous dental vehicle, an anti-caries effective amount of TiF$_4$ and an amount of a chelating agent effective to stabilize the TiF$_4$. Since the TiF$_4$ is stabilized by the chelating agent, the toothpaste of the present invention has the required stability to be sold to the consumer using conventional over-the-counter channels of trade.

Furthermore, the toothpaste of the present invention avoids the low pH at which conventional aqueous TiF$_4$ solutions are employed, and hence the skin irritation arising from the prior art TiF$_4$ solutions is also avoided. This is an important factor in a consumer product, since repeated use and lack of care would make skin irritation more pronounced. The consumer can now use the TiF$_4$-containing toothpaste of the invention on a daily basis instead of being limited to annual treatments with TiF$_4$ by a dentist.

In addition to the advantage of enhanced fluoride uptake, the toothpaste of the invention also forms a protective glaze on the teeth in the form of an organo-metallic complex when the amount of TiF$_4$ is at least about 1.0% by weight, based on the total composition. This glaze renders the teeth more acid-resistant and may desenitize exposed dentin by sealing exposed dentin tubules. This latter effect may protect susceptible teeth against root caries.

The hydrous toothpaste of the invention comprises a chelating agent to stabilize TiF$_4$ in the aqueous medium of the toothpaste and thereby prevent decomposition of the TiF$_4$ and resultant losses of available fluoride and titanium ions. A wide range of chelating agents may be used in the present invention, particularly those containing chelating hydroxy, carboxy and/or sulfonic acid groups, such as for example, ethylene diamine tetraacetic acid, salicyclic acid, citric acid, 2,4 and 2,6-dihydroxybenzoic acids, dihydroxytartaric acid, nitrilotriacetic acid, tartaric acid, 4,5-dihydroxy-1,3-benzenedisulfonic acid, mandelic acid, malic acid, mellitic acids, oxalic acid and acetic acid. The acid groups may be in the form of the free acid or metal salt thereof. Alternatively, the chelating agent may be added in the form of a metal chelate, particularly a di- or trivalent metal chelate. Examples of such metal chelates include complexes of $\beta$-diketones with aluminum and chromium, for example aluminium and chromium triacetylacetonates, and ethylene diamine tetraacetic acid complexes of zinc and copper. It is presently preferred to use tartaric acid or citric acid or their alkali metal salts, or other chelating agents containing both chelating hydroxy and carboxy groups.

The amount of the chelating agent will generally be from about 0.10 to about 15%, preferably from about 0.30 to about 6.0% of the composition. It is presently preferred that the ratio of the chelating agent to the TiF$_4$ be from about 1:1 to about 5:1 or more, preferably from about 2:1 to about 4:1.

The toothpaste of the present invention also comprises an anti-caries effective amount of TiF$_4$. Preferably, the toothpaste will provide at least 250 ppm F to obtain an anti-caries effect and hence the amount of TiF$_4$ in the toothpaste will preferably be at least about 0.04%, such as from about 0.04 to about 2.5%, and most preferably from about 0.12 to about 1.0%.

One preferred embodiment of the invention provides from about 0.10 to about 0.30% of TiF$_4$ and from about 0.10 to about 1.5% of said chelating agent, by weight based on the total composition.

Another preferred embodiment of the invention provides from about 1.0 to about 2.5% TiF$_4$ and from about 1.0 to about 12.5% of said chelating agent, by weight based on the total composition.

The toothpaste of the invention also comprises a dental polishing or abrasive agent. Preferably, a siliceous polishing agent with a particle size of up to about 75 microns is used. As is known, the use of siliceous polishing agents provides a transparent or translucent gel that can be opacified with a pigment, e.g. TiO$_2$, if desired. Alternatively, other dental abrasives can be used, such as calcium carbonate, water-insoluble sodium or potassium metaphosphates, hydrated or anhydrous dicalcium phosphate, calcium pyrophosphate, zirconium silicate or mixtures thereof, in which case an opaque paste is generally obtained. Hydrated silica, SiO$_2$xH$_2$O, is a suitable siliceous polishing agent, where x varies with the method of precipitation and extent of drying. Numerous sources of hydrated silica are available, as described in the CTFA Ingredients Dictionary. It is presently preferred to use silica xerogels, such as described in U.S. Pat. No. 3,538,230, but with particle sizes of up to about 75 microns. Generally, an amount of from about 1 to about 50%, preferably from about 2 to about 20%, of the dental abrasive will be employed. Preferably a xerogel is used having a particle size of from about 25 to about 75 microns, most preferably from about 25 to about 40 microns.

The toothpaste of the invention may also contain surfactants, gelling agents, and other excipients, such as flavoring and coloring agents.

The surfactant is normally a water-soluble non-soap or synthetic organic detergent. Suitable surfactants include the water-soluble salts of higher fatty acid monoglyceride monosulphates (for example sodium hydrogenated coconut fatty acid monoglyceride monosulphate); higher alkyl sulphates (for example sodium lauryl sulphate); alkylarylsulphonates (for example, sodium dodecylbenzenesulphonate); and higher alkyl sulphoacetates (for example, sodium lauryl sulphoacetate). There may also be used the saturated higher aliphatic acyl amides of lower aliphatic amino carboxylic acids having 12 to 16 carbon atoms in the acyl radical and in which the amino acid portion is derived from the lower aliphatic saturated monoaminocarboxylic acids having 2 to 6 carbon atoms, such as the fatty acid amines of glycine, sarcosine, alanine, 3-aminopropanoic acid and valine, particularly the N-lauroyl, myristoyl and palmitoyl sarcosinate compounds. Conventional non-ionic surfactants may also be included if desired. Examples of suitable non-ionic surfactants include the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

The surface-active materials may be present in an amount of from about 0.05 to about 10%, preferably from about 0.5 to about 5%, of the composition.

The toothpaste according to the invention is a gel or paste that may employ a gelling agent, binder or thickener to provide the desired rheological properties. Such agents are known in the art and include the natural and synthetic gums and gum-like materials, such as alkali metal carboxymethyl cellulose, hydroxyethyl carboxymethyl cellulose, polyvinyl pyrrolidone, Irish moss, gum tragacanth, hydroxypropyl methyl cellulose, methyl cellulose, starches, starch glycolates, polyvinyl alcohol, alginates, carob bean gums, and hydrophilic colloidal carboxyvinyl polymers, such as those sold under the trademarks Carbopol 934 and Carbopol 940, diatomaceous earths, bentonite and other natural clays (these also may function as polishing agents), proteinaceous materials, either animal- or vegetable-derived, and synthetic inorganic clays, such as the silicated clays sold under the trademarks Laponite CP and Laponite SP. Certain colloidal silicas such as the aerogels, Syloids 244 and 266 and Aerosil, and pyrogenic silica, sold as Cab-O-Sils, may be used also for thickening or gelling properties. Of course, as with the other constituents of the invention, mixtures thereof may be employed to obtain specially desirable properties in the product. It is presently preferred to use fumed silica or a cellulose gum as the binder or thickener.

The amount of gelling agent or thickener is sufficient to form an extrudable, shape-retaining product which can be squeezed from a tube onto a toothbrush and will not fall between the bristles of the brush but rather will substantially maintain its shape thereon. In almost all cases, no more than about 15% of gelling agent need be used and in most instances from about 1 to about 15% will suffice.

The aqueous dental vehicle comprises a mixture of water and a humectant, such as glycerin, aqueous sorbitol, polyethylene glycol or propylene glycol. The total liquid content is generally in the range from about 20% to about 95%, and typically comprises up to about 40% of water, 0 to about 80% of glycerine, 0 to about 80% of sorbitol and 0 to 20% propylene glycol and/or polyethylene glycol. Preferably, 0 to about 40% of glycerine, 0 to about 60% of sorbitol, and 0 to 10% propylene glycol and/or polyethylene glycol are present. It is presently preferred to use aqueous sorbitol and/or liquid polyethylene glycol as the humectant. Polyethylene glycol has the formula $HO(CH_2CH_2O)_nH$, where n is an integer, such as from about 2 to about 40.

Other materials may be added, such as soluble saccharin, flavoring oils (e.g. oils of spearmint, wintergreen, peppermint), coloring or whitening agents (e.g. titanium dioxide), preservatives (e.g. sodium benzoate), emulsifying agents, silicones, alcohol, menthol, chlorophyll compounds (e.g. sodium copper chlorophyllin), and anti-bacterial agents (e.g. chlorhexidine). These materials, when present, will be in minor amounts, such as up to about 4%, e.g. from about 0.05 to about 3%, in total.

A preferred composition for use in the present invention comprises

| | |
|---|---|
| 10 to 70% | humectant |
| 10 to 30% | deionized water |
| 2 to 20% | siliceous polishing agent |
| 1 to 15% | gelling agent, binder or thickener |
| 1 to 3% | surfactant |
| 0.10 to 1.5% | chelating agent |
| 0.10 to 0.30% | $TiF_4$ |
| 0.5 to 2% | flavorants, sweetener and colorant |

Alternatively, the amount of $TiF_4$ in the above formulation may be from about 1.0 to about 2.5% by weight, based on the total composition, so as to provide an amount of titanium ions effective to form an organometallic protective glaze on the teeth, in which case the amount of chelating agent is preferably from about 1.0 to about 12.5% by weight.

The toothpaste of the invention is prepared in the usual manner by mixing the ingredients in the dry state or as slurries or solutions. The pH of the toothpaste will generally be from between about 3.5 and about 5.5.

In a preferred embodiment of the invention, the $TiF_4$ is admixed with an aqueous solution of the chelating agent to solubilize the $TiF_4$, and then the remaining ingredients are combined with the mixture of $TiF_4$ and the chelating agent.

The present invention is illustrated in terms of its preferred embodiments in the examples that follow. In this specification and claims, all parts and percentages are by weight, unless otherwise stated.

EXAMPLE 1

| | PERCENT |
|---|---|
| PEG-8 (CFTA)* | 3.00 |
| Sorbitol (70% aqueous solution) | 56.54 |
| Deionized water | 20.00 |
| Titanium tetrafluoride | 0.16 |
| Sodium Citrate | 0.50 |
| Fumed silica | 12.00 |
| Sodium carboxymethylcellulose | 0.65 |
| Hydrated silica | 5.00 |
| Sodium lauryl sulfate | 1.15 |
| Flavor | 0.75 |
| Sodium saccharin | 0.25 |

*PEG-8 (CTFA) is a polyethylene glycol of the formula $H(OCH_2CH_2)_nOH$, where n has an average value of 8.

A toothpaste was prepared from the above ingredients as follows.

The chelating agent was dissolved in water and the $TiF_4$ was added and solubilized, after which sorbitol and sodium saccharin were added. Sodium carboxymethyl cellulose was dispersed in the PEG-8 and then added to the above mixture and allowed to hydrate for 30 minutes. The hydrated mucilage was transferred to a double planetary mixer equipped with vacuum and mixed 10 minutes at 28 inches vacuum. Fumed silica and hydrated silica were added over 15 minutes at atmospheric pressure and then mixed for 15 minutes at 28 inches vacuum. The entire batch was then thinned down with the remainder of the sorbitol over a 20 minute period and mixed for 30 minutes. The flavor was added and mixed for 10 minutes at 28 inches vacuum. The surfactant was added at atmospheric pressure with the mixer off. The vacuum was raised to 28 inches and the batch was mixed for 15 minutes. A translucent gel toothpaste was obtained, having a pH of 5.2.

Samples of the toothpaste of Example 1, as well as samples similarly prepared with the same concentration of $TiF_4$ but with 0.17%, 0.34%, and 0.68% of sodium citrate, were stored at 25° and 37° C. for three months. Storage at 37° C. is a form of accelerated aging such that storage for three months at 37° C. usually represents three years' storage at room temperature (25° C.). The storage data are reported in Table 1, which follows:

TABLE I

STABILITY OF TOOTHPASTE AT DIFFERENT CONCENTRATIONS OF SODIUM CITRATE

| | SODIUM CITRATE (%) | | | | | | | |
|---|---|---|---|---|---|---|---|---|
| | 0.17 | | 0.34 | | 0.50 | | 0.68 | |
| | TOTAL | FREE | TOTAL | FREE | TOTAL | FREE | TOTAL | FREE |
| FLUORIDE ION (ppm)* | | | | | | | | |
| Initial | 974 | 900 | 1026 | 915 | 1030 | 928 | 1033 | 914 |
| 1 Mo. RT | 931 | 814 | 996 | 839 | 1030 | 914 | 1010 | 901 |
| 37° C. | 958 | 811 | 990 | 844 | 1019 | 915 | 992 | 911 |
| 2 Mo. RT | 970 | 931 | 999 | 937 | 1023 | 977 | 1005 | 965 |
| 37° C. | 968 | 931 | 1012 | 924 | 1008 | 969 | 1002 | 956 |
| 3 Mo. RT | 990 | 998 | 989 | 996 | 985 | 890 | 1000 | 923 |
| 37° C. | 997 | 989 | 963 | 939 | 1002 | 894 | 987 | 908 |
| TITANIUM ION (ppm) | | | | | | | | |
| Initial | 633 | 452 | 630 | 412 | 632 | 452 | 639 | 516 |
| 1 Mo. RT | 625 | 456 | 620 | 458 | 641 | 475 | 629 | 455 |
| 37° C. | 646 | 453 | 635 | 490 | 625 | 471 | 633 | 460 |
| 2 Mo. RT | 622 | 465 | 624 | 459 | 635 | 433 | 628 | 425 |
| 37° C. | 617 | 470 | 632 | 462 | 639 | 477 | 622 | 452 |
| 3 Mo. RT | 617 | 455 | 632 | 455 | 631 | 430 | 630 | 423 |
| 37° C. | 620 | 465 | 631 | 448 | 621 | 429 | 624 | 440 |

*(Reported values are ±10%)

Prior to mixing the ingredients together to form the toothpaste, the composition contained 1000 ppm fluoride and 633 ppm titanium ions. After mixing, the total and free fluoride ions were as set forth in Table 1 under the term "Initial". After three months' storage, the total and free fluoride ions were almost unchanged even under the accelerated aging conditions, thus demonstrating extraordinary stability. Table 1 also shows acceptable total and free titanium ions after aging. The pH of the four toothpastes tested were:

| Sodium Citrate % | pH |
|---|---|
| 0.17 | 4.50 |
| 0.34 | 4.85 |
| 0.50 | 5.20 |
| 0.68 | 5.20 |

The $TiF_4$- containing toothpaste of the invention is thus storage-stable at a pH of 5.2 despite the instability of $TiF_4$ in aqueous media at a pH above 3.0. In addition, the composition of the present invention also provides increased titanium uptake as well.

We claim:

1. An extrudable, shape-retaining aqueous toothpaste which comprises an anti-caries effective amount in the range of from about 0.04 to about 2.5% of $TiF_4$, a dental polishing or abrasive agent, a chelating agent in an amount of from about 0.10 to about 15% and effective to stablize the $TiF_4$, and an aqueous dental vehicle, said aqueous toothpaste having a pH of from about 3.5 to about 5.5, the percentages being percentages by weight based on the total weight of the toothpaste.

2. The aqueous toothpaste according to claim 1, wherein the weight ratio of said chelating agent to said $TiF_4$ is from about 1:1 to about 5:1.

3. The aqueous toothpaste according to claim 1, wherein said dental vehicle comprises water, a humectant and a gelling agent or thickener.

4. The aqueous toothpaste according to claim 1, wherein said chelating agent is selected from the group consisting of chelating agents having one or more chelating hydroxy, carboxy or sulfonic acid groups and metal chelates.

5. The aqueous toothpaste according to claim 4, wherein said chelating agent is selected from the group consisting of ethylenediaminetetraacetic acid, salicyclic acid, citric acid, 2,4 and 2,6-dihydroxybenzoic acids, dihydroxy tartaric acid, nitrilotriacetic acid, tartaric acid, 4,5-dihydroxy-1,3-benzenedisulfonic acid, mandelic acid, malic acid, mellitic acids, oxalic acid, acetic acid and metal chelates or a mixture of two or more thereof.

6. The aqueous toothpaste according to claim 1, wherein said chelating agent contains chelating hydroxy and carboxy groups.

7. The aqueous toothpaste according to claim 1, which comprises from about 0.10 to about 0.30% of $TiF_4$ and from about 0.10 to about 1.5% of said chelating agent, by weight based on the total composition.

8. The aqueous toothpaste according to claim 1, which comprises from about 1.0 to about 2.5% $TiF_4$ and from about 1.0 to about 12.5% of said chelating agent, by weight based on the total composition.

9. The aqueous toothpaste according to claim 6, wherein the chelating agent is tartaric acid, citric acid or an alkali metal salt thereof.

10. The aqueous toothpaste according to claim 7 wherein the chelating agent is tartaric acid, citric acid or an alkali metal salt thereof.

11. The aqueous toothpaste according to claim 8, wherein the chelating agent is tartaric acid, citric acid or an alkali metal salt thereof.

12. The aqueous toothpaste according to claim 1, wherein the polishing agent is a siliceous polishing agent.

13. The aqueous toothpaste according to claim 9, wherein the polishing agent is a siliceous polishing agent.

14. The aqueous toothpaste according to claim 10, wherein the polishing agent is a siliceous polishing agent.

15. The aqueous toothpaste according to claim 11, wherein the polishing agent is a siliceous polishing agent.

* * * * *